(12) United States Patent
Yanagi et al.

(10) Patent No.: US 8,529,953 B2
(45) Date of Patent: Sep. 10, 2013

(54) PROCESS FOR PRODUCTION OF SPHERICAL MICROPARTICLES COMPRISING TAMSULOSIN HYDROCHLORIDE

(75) Inventors: Toshihiro Yanagi, Osaka (JP); Yoshitaka Iwakura, Osaka (JP); Hisaya Sangawa, Osaka (JP); Yasufumi Okamura, Osaka (JP)

(73) Assignee: Sawai Pharmaceutical Co., Ltd., Osaka (JP)

( * ) Notice: Subject to any disclaimer, the term of this patent is extended or adjusted under 35 U.S.C. 154(b) by 180 days.

(21) Appl. No.: 13/001,393

(22) PCT Filed: Jun. 29, 2009

(86) PCT No.: PCT/JP2009/002981
§ 371 (c)(1),
(2), (4) Date: Dec. 23, 2010

(87) PCT Pub. No.: WO2010/001574
PCT Pub. Date: Jan. 7, 2010

(65) Prior Publication Data
US 2011/0104270 A1 May 5, 2011

(30) Foreign Application Priority Data
Jul. 1, 2008 (JP) .................................. 2008-172828

(51) Int. Cl.
*A61K 9/14* (2006.01)
*A61K 9/20* (2006.01)
*A61K 9/00* (2006.01)
*A61K 31/18* (2006.01)

(52) U.S. Cl.
USPC ............ 424/489; 424/464; 424/400; 514/603

(58) Field of Classification Search
USPC ......................... 424/464, 400, 490; 514/603
See application file for complete search history.

(56) References Cited

U.S. PATENT DOCUMENTS 4,772,475 A 9/1988 Fukui et al.
5,384,130 A 1/1995 Kamada
(Continued)

FOREIGN PATENT DOCUMENTS

JP 61-213201 A 9/1986
JP 62-000009 A 1/1987
(Continued)

OTHER PUBLICATIONS

Bultmann, ."Multiple compaction of microcrystalline cellulose in a roller compactor" in European Journal of Pharmaceutics and Biopharmaceutics; vol. 54, Issue 1, Jul. 2002, pp. 59-64.*

(Continued)

*Primary Examiner* — Blessing Fubara
(74) *Attorney, Agent, or Firm* — Sughrue Mion, PLLC

(57) ABSTRACT

The present invention provides a method for producing spherical fine particles containing tamsulosin hydrochloride, the method includes the steps of: (1) mixing and stirring tamsulosin hydrochloride (a), microcrystalline cellulose (b), and water until a mixture of the component (a) and the component (b) is uniformly impregnated with the water; (2) granulating the mixture obtained in step (1) using an stirring granulator whose peripheral speed is set to be 5.5 to 9.0 m/s; and (3) drying the granules obtained in step (2). The present invention also provides spherical fine particles obtained according to the method, coated fine particles obtained by applying a coating to the spherical fine particles, and an orally disintegrating tablet containing the coated fine particles.

6 Claims, 5 Drawing Sheets

Test Example 1

(56) References Cited

U.S. PATENT DOCUMENTS

| | | |
|---|---|---|
| 6,242,008 B1 | 6/2001 | Akiyama et al. |
| 6,692,768 B1 | 2/2004 | Ishibashi et al. |
| 2003/0147948 A1* | 8/2003 | Shinoda et al. ............... 424/465 |
| 2004/0043964 A1 | 3/2004 | Gomi et al. |
| 2005/0106253 A1* | 5/2005 | Platteeuw ................... 424/471 |

FOREIGN PATENT DOCUMENTS

| | | |
|---|---|---|
| JP | 05-092918 A | 4/1993 |
| JP | 06-056700 A | 3/1994 |
| JP | 07-165568 A | 6/1995 |
| JP | 07-173050 A | 7/1995 |
| JP | 09-165329 A | 6/1997 |
| JP | 09-295947 A | 11/1997 |
| JP | 2000-504309 A | 4/2000 |
| JP | 2000-128774 A | 5/2000 |
| JP | 2002-338454 A | 11/2002 |
| JP | 2005-213220 A | 8/2005 |
| JP | 2008-050284 A | 3/2008 |
| WO | 02/36168 A1 | 5/2002 |
| WO | 03/009831 A1 | 2/2003 |
| WO | 2009/040388 A1 | 4/2009 |

OTHER PUBLICATIONS

Woodruff and Nuessle, "Effect of Processing Variables on Particles Obtained by Extrusion-Spheronization Processing" in Journal of Pharmaceutical Sciences, vol. 61, No. 5, May 1972.*

* cited by examiner

Test Example 2

Example 1

PROCESS FOR PRODUCTION OF SPHERICAL MICROPARTICLES COMPRISING TAMSULOSIN HYDROCHLORIDE

TECHNICAL FIELD

The present invention relates to a method for producing spherical fine particles that contain tamsulosin hydrochloride and to coated fine particles that are used in an orally disintegrating tablet and prepared by applying a coating to the spherical fine particles obtained according to the method.

BACKGROUND ART

Pharmaceutical preparations with a controlled release of a medicinal component have been developed for various purposes such as extending pharmaceutical effects, preventing side effects, and preventing medicinal components from being decomposed by gastric acid. Usually, controlled release oral preparations are mostly formulated into tablets and capsules. Meanwhile, there has recently been a growing need for orally disintegrating tablets that can be taken without water to enhance compliance of elderly patients, patients with dysphagia, and patients who are allowed to take only limited amounts of water.

For example, tamsulosin hydrochloride, which is a drug for urologic diseases, is rapidly absorbed into the body after administration and therefore sustained-release capsules were developed at first to avoid side effects such as orthostatic hypotension. Sustained-release orally disintegrating tablets have been developed therefor and are now commercially available.

When tamsulosin hydrochloride or a like medicinal component the release of which from a pharmaceutical preparation needs to be controlled is formulated as an orally disintegrating tablet, medicinal component-containing fine particles that are designed to release the medicinal component in a controlled manner are produced first and then the fine particles are dispersed in a tablet. From the viewpoint of suppressing a rough texture that is felt upon oral administration, it is desirable to make the particle diameter of controlled-release fine particles that contain a medicinal component as small as possible, and it is generally thought that the upper limit of the average particle diameter is about 350 to about 400 μm.

In general, in the production methods of controlled-release pharmaceutical preparations, a technique by which pharmaceutical preparations such as tablets, granules, and those that contain a medicinal component are coated with a sustained-release film and/or an enteric film is broadly applied to various types of drugs because the operation is simple and the properties of releasing a medicinal component is easily controlled.

When such a coating is applied to particles for an orally disintegrating tablet, coated particles are required to have a very small average particle diameter of less than 400 μm, and therefore it is necessary first to produce medicinal component-containing fine particles that have a shape as spherical as possible, a uniform particle size, and an average particle diameter of less than 250 μm in order to efficiently apply thereto a coating of a high-quality film layer.

The following techniques are known as conventional production methods of medicinal component-containing fine particles.

Patent Literature 1 (JP 62-9A) discloses a technique to obtain medicinal component-containing particles by adding microcrystalline cellulose and a release-controlling agent to tamsulosin hydrochloride and granulating the mixture. The medicinal component-containing particles are applied to a capsule for the sustained-release of tamsulosin hydrochloride. However, the particle size range of the particles is 100 to 1500 μm and there are a considerable number of large particles exceeding 1000 μm are contained, and it is therefore difficult to apply such particles to an orally disintegrating tablet.

Patent Literature 2 (JP 07-165568 A) discloses a method for obtaining medicinal component-containing particles by kneading a mixture of the active ingredient idebenone, crystalline cellulose, and the like, granulating the mixture with an extrusion granulator, and spheronizing the granules with a spheronizer. However, granules that pass through a 60 mesh (i.e., particles smaller than 250 μm) are barely obtained according to this method. The reason for this is easily presumable from the fact that the spheronizer is of a nature not suitable for preparing fine particles smaller than 500 μm.

Patent Literature 3 (JP 06-56700A) discloses a coated core for fine granules obtained by subjecting a principal ingredient and crystalline cellulose to stirring granulation. However, the coated core obtained according to this document has a broad particle size distribution over the 75 to 500 μm range. It may not be possible to provide a coating that enables a highly reproducible release of the medicinal component when coated fine particles for an orally disintegrating tablet, which should have an average particle diameter of no more than about 350 to about 400 μm, are prepared.

Patent Literature 4 (JP 2000-504309 A) discloses a method that performs high-speed stirring granulation on a mixture of a medicinal component and an excipient. However, the obtained granules have a large particle diameter of 500 μm or greater and it is very difficult to apply the granules to an orally disintegrating tablet.

As described above, a technique is not yet established for obtaining medicinal component-containing fine particles that are suitable for an orally disintegrating tablet and that have a sufficiently small particle diameter even after being coated, a uniform particle diameter, and a nearly spherical shape, and therefore demand exists for a method for conveniently obtaining such spherical fine particles.

CITATION LIST

Patent Literature 1: JP 62-9 A
Patent Literature 2: JP 07-165568 A
Patent literature 3: JP 06-56700 A
Patent literature 4: JP 2000-504309 A

SUMMARY OF INVENTION

Technical Problem

An object of the present invention is to provide a method for producing tamsulosin hydrochloride-containing spherical fine particles that are suitable for an orally disintegrating tablet and have a narrow particle size distribution.

Another object of the present invention is to provide spherical fine particles obtained according to the above method, coated fine particles obtained by applying a coating to the spherical fine particles, and an orally disintegrating tablet containing the coated fine particles.

Solution to Problem

The inventors conducted extensive research to solve the problems described above. As a result, the inventors surprisingly found that stirring tamsulosin hydrochloride, microcrystalline cellulose, and water until the mixture of tamsulosin hydrochloride and microcrystalline cellulose is uniformly impregnated with water and then granulating the mixture using a stirring granulator whose peripheral speed is set to be within a specific range yield spherical fine particles having a narrow particle size distribution. The inventors, having conducted further research based on this finding, accomplished the present invention.

The present invention provides a method for producing spherical fine particles containing tamsulosin hydrochloride, spherical fine particles obtained according to the method, coated fine particles obtained by applying a coating to the spherical fine particles, and an orally disintegrating tablet containing the coated fine particles, as described below.

Item 1. A method for producing spherical fine particles containing tamsulosin hydrochloride, the method including the steps of:
(1) mixing and stirring tamsulosin hydrochloride (a), microcrystalline cellulose (b), and water until a mixture of the component (a) and the component (b) is uniformly impregnated with the water;
(2) granulating the mixture obtained in step (1) using an stirring granulator whose peripheral speed is set to be 5.5 to 9.0 m/s; and
(3) drying the granules obtained in step (2).

Item 2. The production method according to item 1, wherein in step (1), after dry-blending the tamsulosin hydrochloride (a) and the microcrystalline cellulose (b), water is added, and mixing and stirring is performed.

Item 3. The production method according to item 1 or 2, wherein in step (1), mixing and stirring is performed using a stirring granulator whose peripheral speed is set to be 1.0 to 4.0 m/s.

Item 4. The production method according to any one of items 1 to 3, wherein in step (1), the water is added in an amount of 70 to 110 parts by weight per 100 parts by weight of the mixture of the component (a) and the component (b).

Item 5. The production method according to any one of items 1 to 4, wherein spherical fine particles having a particle diameter of from 75 μm to less than 250 μm account for 80 wt % or greater of the entire spherical fine particles obtained.

Item 6. The production method according to any one of items 1 to 5, wherein spherical fine particles having a particle diameter of from 106 μm to less than 150 μm account for 50 wt % or greater of the entire spherical fine particles obtained.

Item 7. The production method according to any one of items 1 to 6, wherein the obtained spherical fine particles contain the tamsulosin hydrochloride (a) in an amount of 30 wt % or less.

Item 8. Spherical fine particles containing tamsulosin hydrochloride, obtained according to the method of any of items 1 to 7.

Item 9. Coated fine particles prepared by applying a coating to the spherical fine particles of item 8.

Item 10. The coated fine particles according to item 9, wherein the coating is a sustained-release coating and/or an enteric coating.

Item 11. An orally disintegrating tablet containing the coated fine particles of item 9 or 10.

Advantageous Effects of Invention

According to the present invention, the following effects are obtained.

(1) According to the present invention, tamsulosin hydrochloride-containing spherical fine particles that are suitable for an orally disintegrating tablet and have a narrow particle size distribution are obtained.

(2) Since the tamsulosin hydrochloride-containing spherical fine particles obtained by the method of the invention are nearly spherical and have a narrow particle size distribution, they are suitable for receiving a sustained-release, enteric, or like coating.

(3) The application of a coating to the spherical fine particles obtained by the method of the invention allows coated fine particles that are suitable for an orally disintegrating tablet to be produced. Since the particle diameter of the coated fine particles is sufficiently small, the use of the coated fine particles allows an orally disintegrating tablet with which a rough texture is barely felt upon oral administration to be produced.

(4) Moreover, good content uniformity is ensured with the spherical fine particles even though the tamsulosin hydrochloride content of a pharmaceutical preparation is low.

DESCRIPTION OF EMBODIMENTS

Figure 1:
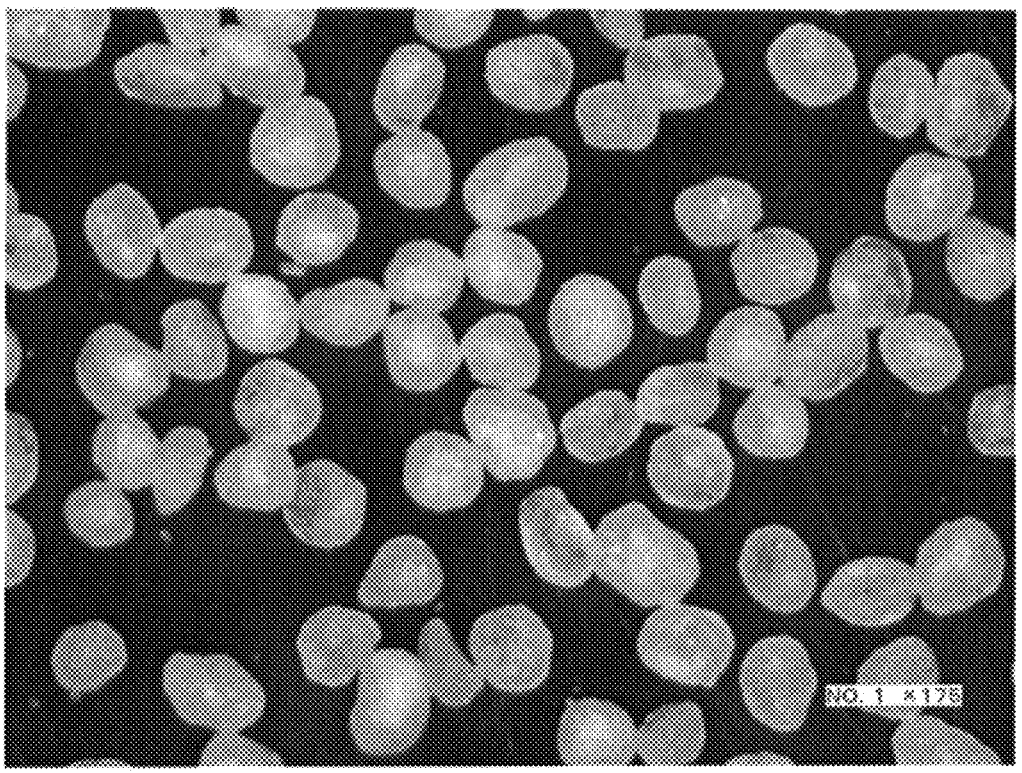
FIG. 1 is a micrograph (175-fold magnification) of the fine particles obtained in Test Example 1(A).
Figure 2:
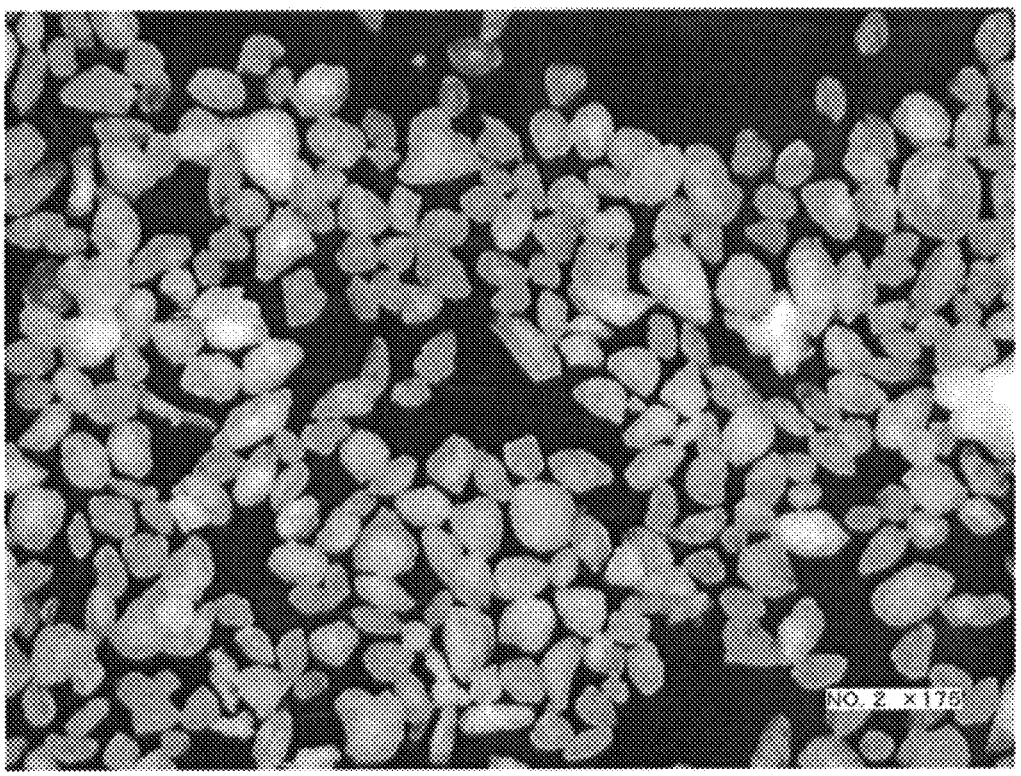
FIG. 2 is a micrograph (175-fold magnification) of the fine particles obtained in Test Example 1(B).
Figure 3:
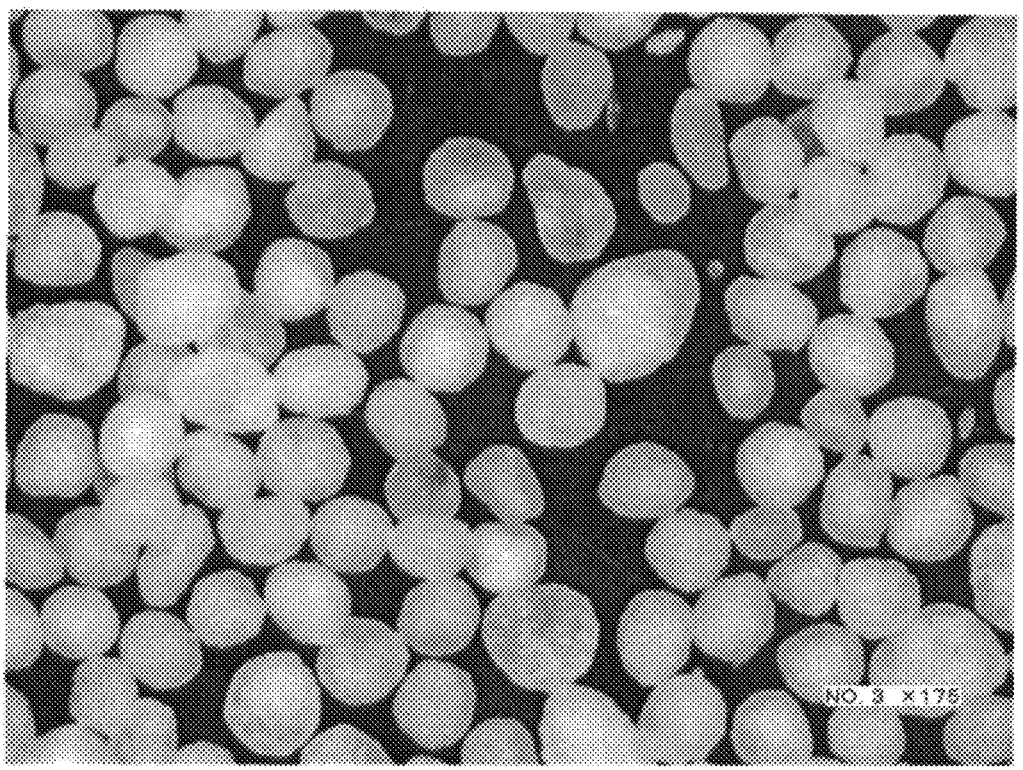
FIG. 3 is a micrograph (175-fold magnification) of the fine particles obtained in Test Example 1(C).
Figure 4:
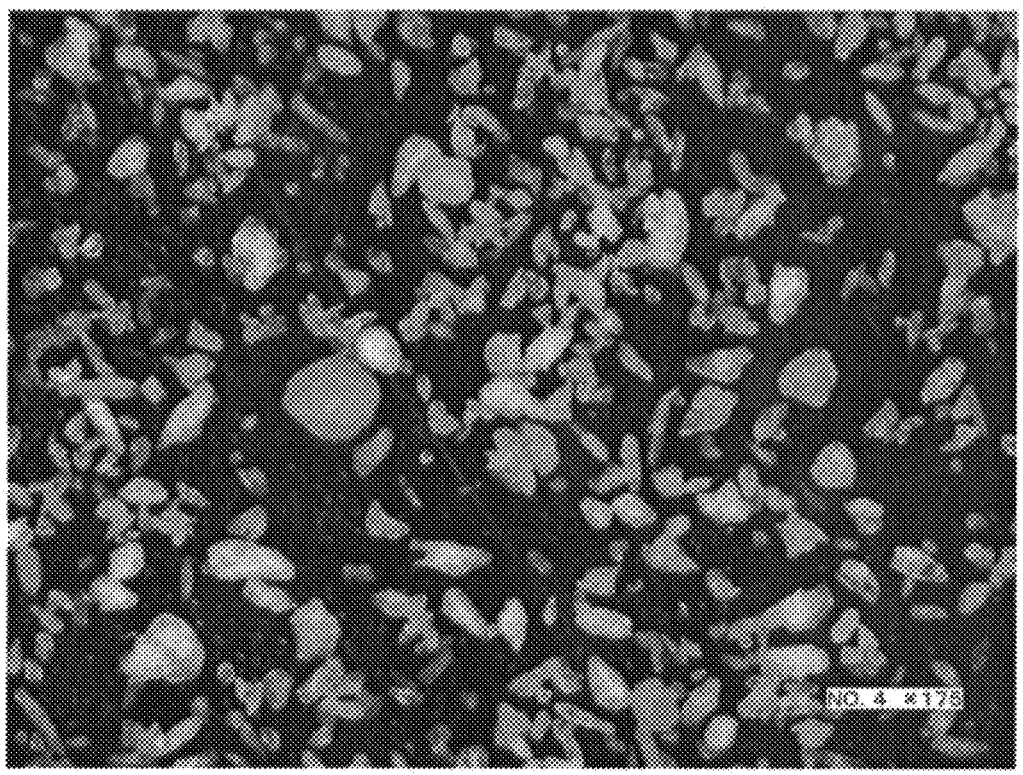
FIG. 4 is a micrograph (175-fold magnification) of the fine particles obtained in Test Example 1(D).
Figure 5:
FIG. 5 is a micrograph (50-fold magnification) of the fine particles obtained in Test Example 1(E).

Production Method of Spherical Fine Particles Containing Tamsulosin Hydrochloride The method for producing spherical fine particles containing tamsulosin hydrochloride of the present invention includes the steps of: (1) mixing and stirring tamsulosin hydrochloride (a), microcrystalline cellulose (b), and water; (2) granulating the mixture obtained in step (1); and (3) drying the granules obtained in step (2).

Step (1)

This is a step of mixing and stirring tamsulosin hydrochloride (a), microcrystalline cellulose (b), and water until a mixture of the component (a) and the component (b) is uniformly impregnated with the water.

Tamsulosin hydrochloride (a) is the active ingredient of an orally disintegrating tablet containing the fine particles of the present invention, lowers the prostatic intraurethral pressure by blocking the $\alpha_1$ receptor in the urethra and the prostate gland, and functions to ameliorate urinary disturbances accompanied by benign prostatic hyperplasia. Tamsulosin hydrochloride (a), the chemical name of which is 5-{(2R)-2-[2-(2-ethoxyphenoxy)ethylamino]propyl}-2-methoxybenzenesulfonamide monohydrochloride, is a white crystal.

Additionally, the tamsulosin hydrochloride (a) may be used in combination with other medicinal components.

It is usually preferable that the tamsulosin hydrochloride (a) content of the obtained spherical fine particles is about 30 wt % or less and more preferably about 0.001 to about 10 wt %.

Microcrystalline cellulose (b) is a white powdery material and is used as an excipient of the spherical fine particles obtained according to the present invention. It is preferable that the microcrystalline cellulose (b) has a particle size smaller than the particle diameter of the spherical fine particles to be obtained, for example, an average particle diameter of about 10 to about 80 μm and a bulk density of about 0.20 to about 0.40 g/cm$^3$. As for the microcrystalline cellulose (b), "Ceolus (registered trademark) PH-101", "PH-101D", or "PH-F20JP" manufactured by Asahi Kasei Chemicals Corporation or the like may be used. Among such examples, "PH-101" is preferable.

As long as there is no adverse pharmaceutical effect, excipients other than the microcrystalline cellulose (b) may be used in combination. Examples of such excipients include corn starch and like starches; lactose, sucrose, mannitol, erythritol, sorbitol, maltitol, calcium citrate, calcium phosphate, anhydrous calcium hydrogen phosphate, magnesium carbonate, calcium carbonate, and magnesium aluminometasilicate; and the like. Among such excipients, those that scarcely absorb water and barely react with other ingredients are desirable.

A binder may be contained in water that is added in step (1). Examples of usable binders include maltose, trehalose, sorbitol, maltitol, glucose, xylitol, erythritol, mannitol, and like sugars; polyvinyl pyrrolidone, copolyvidon, polyvinyl alcohol, hydroxypropylcellulose, hypromellose, and like water-soluble polymers.

In step (1), when tamsulosin hydrochloride (a), microcrystalline cellulose (b), and water are mixed and stirred, it is preferable that tamsulosin hydrochloride and microcrystalline cellulose and other optional medicinal components and excipients are thy-blended first to form a powdery mixture, then water is added, and mixing and stirring is performed until the powdery mixture is uniformly impregnated with water.

Here, the state denoted by the phrase "the powdery mixture uniformly impregnated with water" refers to a state in which water is absorbed into the entire powdery mixture and no large mass or fine particles can be observed.

The mixing and stirring operation in step (1) may be performed with a commonly used granulator such as a mixer, a kneading granulator, or a stirring granulator. In particular, it is desirable to use a stirring granulator because it can be used throughout the powder mixing in step (1) and the granulation in step (2). When a stirring granulator is used, it is preferable to keep the peripheral speed low by controlling the revolutions of the agitator until the powdery mixture is uniformly impregnated with water. It is usually desirable that the peripheral speed until the powdery mixture is uniformly impregnated with water is within the range of about 1.0 to about 4.0 m/s.

In the present specification, the peripheral speed is defined by the following formula:

Peripheral speed (m/s)=Diameter (m) of stirring vessel×π×Number of revolutions (rpm)×(1/60)

The revolving speed of the chopper of a stirring granulator may be suitably controlled such that coarse particles are not generated. Since coarse particles are likely to be generated especially until the powdery mixture is uniformly impregnated with water, it is desirable to keep the revolving speed high.

Preferable examples of stirring granulators for use in the present invention include a "high-speed mixer" (trade name, manufactured by Fukae Powtec) and a "vertical granulator" (trade name, manufactured by Powrex Corporation).

Water may be added an unlimited number of times, but in order to prevent particle agglomeration and to attain a uniform particle diameter, it is desirable to add the necessary amount of water at once in step (1).

The amount of water may vary depending on the capacity of a stirring granulator or a like apparatus, drying conditions, and other factors but usually it is preferably about 70 to about 110 parts by weight and more preferably about 70 to about 90 parts by weight per 100 parts by weight of the powdery mixture.

Stirring step (1) is usually performed at room temperature and the time may be suitably determined according to the production scale.

Step (2)

This is a step for granulating the mixture obtained in step (1) using a stirring granulator whose peripheral speed is set to be about 5.5 to about 9.0 m/s.

The spherical fine particles of the present invention are obtained by adding water to a powdery mixture of tamsulosin hydrochloride and microcrystalline cellulose and, as necessary, optional components, and stirring the powdery mixture at a low speed until the powdery mixture is uniformly impregnated with water in step (1) and then performing granulation while stirring using a stirring granulator whose peripheral speed is set to be and kept at about 5.5 to about 9.0 m/s in step (2).

Granulation step (2) is usually performed at room temperature and the time may be suitably determined according to the production scale.

In the production method of the present invention, it is convenient and thus desirable to use a stirring granulator throughout the powder mixing and the uniform water impregnation in step (1) and the granulation operation in step (2). In this case, it is preferable that stirring is performed while keeping the peripheral speed low within a range of, for example, about 1.0 to about 4.0 m/s until water spreads uniformly over the powdery mixture and then granulation is performed while keeping it within a range of about 5.5 to about 9.0 m/s. The peripheral speed may be changed unlimited number of times and this includes a case where the peripheral speed is gradually increased in a step-wise manner and eventually set to be within a range of about 5.5 to about 9.0 m/s. Throughout the steps (1) and (2), the revolving speed of the chopper of a stirring granulator may be suitably controlled such that coarse particles are not generated. Since coarse particles are likely to be generated especially until the powdery mixture is uniformly impregnated with water, it is desirable to set the revolving speed high so as to avoid generation of coarse particles.

Step (3)

This is a step for drying the granules obtained in step (2). It is preferable to carry out the drying step usually at a temperature of about 60 to about 80° C.

Apparatuses for use in the drying step are not particularly limited. A tray dryer, a rotary fluid-bed apparatus, a fluid-bed granulator/dryer, or the like may be selected, and among such dryers, a fluid-bed granulator/dryer is desirable. The drying time is, for example, when a fluid-bed granulator/dryer is used, usually preferably about 30 to about 90 minutes to sufficiently dry the spherical fine particles.

The tamsulosin hydrochloride-containing spherical fine particles thus obtained are nearly spherical and have a narrow particle size distribution. It is preferable that spherical fine particles that have a particle diameter of from 75 μm to less than 250 μm account for 80 wt % or greater of the entire spherical fine particles. It is more preferable that spherical fine particles that have a particle diameter of from 106 μm to less than 150 μm account for 50 wt % or greater of the entire particles.

Coated Fine Particles

Coated fine particles can be obtained by applying a coating to the tamsulosin hydrochloride-containing spherical fine particles obtained by the production method of the present invention. Since controlled-release fine particles with a desired medicinal component releasability can be obtained, such a coating is preferably a sustained-release coating and/or an enteric coating.

The components of the sustained-release coating/the enteric coating are not particularly limited, and polymers that dissolve in the intestines, polymers that dissolve in the stomach, water-soluble polymers, water-insoluble polymers, plasticizers, surfactants, and the like may be used in a suitable combination as necessary.

Examples of polymers that dissolve in the intestines include cellulose acetate phthalate, hypromellose phthalate, hypromellose acetate succinate, methacrylic acid copolymer L, methacrylic acid copolymer LD, methacrylic acid copolymer S, and the like. Examples of polymers that dissolve in the stomach include polyvinyl acetal diethylamino acetate, amino alkyl methacrylate copolymer E, and the like. Examples of water-soluble polymers include hydroxypropylcellulose, polyvinyl alcohol, povidone, hypromellose, and the like. Examples of water-insoluble polymers include ethylcellulose, aminoalkyl methacrylate copolymer RS, ethyl acrylate-methyl methacrylate copolymer, and the like. Examples of plasticizers include macrogols, triethyl citrate, and the like. Surfactants include polysorbate 80 and the like.

Apparatuses for use in the coating step are not particularly limited, and a conventional fluid-bed granulator, a rotary fluid-bed granulator, a centrifugal rotary granulator/coating device, a hybrid granulator/coating device, or the like may be used.

Orally Disintegrating Tablet

This is an orally disintegrating tablet containing the above-described coated fine particles. For example, the orally disintegrating tablet may be produced in the following manner. A mixture of the coated fine particles and a desired additive is directly, or after subjecting it to granulation, particle size regulation, or like processing, mixed with powdered magnesium aluminometasilicate and then pressed in a conventional manner. Tablet presses are not limited as long as they are usable in the production of pharmaceutical preparations. For example, a rotary tablet press, a single-punch tablet press, or the like may be used.

In the present invention, the coated fine particles may be granulated in combination with a desired additive prior to being pressed. Additives are not particularly limited, and excipients, disintegrators, binders, and the like may be used in a suitable combination. When the mouth smoothness is taken into consideration, tablets containing a water soluble or hydrophilic additive are preferable.

As for excipients, for example, lactose, mannitol, sorbitol, xylitol, trehalose, cyclodextrin, corn starch, sucrose, crystalline cellulose, anhydrous calcium hydrogen phosphate, calcium carbonate, and the like may be used in a suitable combination. D-mannitol is particularly preferable.

Examples of disintegrators include crystalline cellulose, crospovidone, carmellose, low-substituted hydroxypropylcellulose, carmellose calcium, croscarmellose sodium, sodium carboxymethyl starch, partially pregelatinized starch, hydroxypropyl starch, and the like. Low-substituted hydroxypropylcellulose is particularly preferable.

As for binders, for example, maltose, trehalose, sorbitol, maltitol, glucose, xylitol, erythritol, mannitol, and like sugars; polyvinyl pyrrolidone, copolyvidon, polyvinyl alcohol, hydroxypropylcellulose, hypromellose, and like water-soluble polymers; and the like may be used. Hydroxypropylcellulose is particularly preferable.

The orally disintegrating tablet of the present invention may further contain, in addition to the granules containing the coated fine particles, sweeteners, taste improvers, fluidizers, lubricants, flavoring agents, coloring agents, and the like that are generally used in the production of pharmaceutical preparations and food products.

Examples of sweeteners include mannitol, starch sugar, hydrogenated maltose, starch syrup, sorbitol, sucrose, fructose, lactose, honey, xylitol, erythritol, sorbitol, saccharin, glycyrrhiza and glycyrrhiza extracts, glycyrrhizic acid, sweet hydrangea leaf, aspartame, stevia, thaumatin, acesulfame K, sodium citrate, sucralose, and the like.

Examples of taste improvers include citric acid, sodium citrate, tartaric acid, DL-malic acid, glycine, DL-alanine, and the like.

Examples of fluidizers and/or lubricants include hydrated silicon dioxide, light anhydrous silicic acid, calcium silicate, magnesium stearate, calcium stearate, stearic acid, talc, sodium lauryl sulfate, hydrogenated vegetable oil, microcrystalline wax, sucrose fatty acid ester, polyethylene glycol, and the like.

Examples of flavoring agents include strawberry flavors, lemon flavors, lemon lime flavors, orange flavors, l-menthol, peppermint oil, and the like.

Examples of coloring agents include yellow ferric oxide, red ferric oxide, food tar pigments, naturally-occurring pigments, and the like.

A preferable example of magnesium aluminometasilicate is a product of Fuji Chemical Industry Co., Ltd. (trade name "Neusilin" (registered trademark)). Among the various types of Neusilin that are different according to the bulk specific volume, the water content, the particle shape, and the pH of a 4 wt % aqueous slurry, the "Neusilin UFL2" is the most preferable.

Accordingly, an orally disintegrating tablet containing coated fine particles to which controlled releasability is imparted by applying a coating to tamsulosin hydrochloride-containing spherical fine particles can be prepared.

EXAMPLES

The present invention shall be described in more detail below by way of test examples, examples, and experimental examples although the present invention is not limited by any of these examples.

Test Example 1

Through the operations (A) to (E) presented below, 5 kinds of fine microcrystalline cellulose particles were obtained.

(A): 1000 g of microcrystalline cellulose ("Ceolus (registered trademark) PH-101", manufactured by Asahi Kasei Chemicals Corporation) and 850 g of water were introduced into a high-speed stirring granulator (trade name "vertical granulator VG-25", manufactured by Powrex Corporation)

and stirred at a peripheral speed of 2.1 m/s (the number of revolutions of the agitator: 100 rpm) for 8 minutes and then at a peripheral speed of 6.3 m/s (the number of revolutions of the agitator: 300 rpm) for 15 minutes. Thereafter, the resulting granules were dried with a fluid-bed granulator/dryer at 70° C. for 1 hour, thereby giving fine particles.

(B): Fine particles were produced according to the same procedures performed under the same conditions as in (A) except that the peripheral speed was maintained at 2.1 m/s (the number of revolutions of the agitator: 100 rpm) from the beginning to the termination of revolution.

(C): Fine particles were produced according to the same procedures performed under the same conditions as in (A) except that the peripheral speed was maintained at 6.3 m/s (the number of revolutions of the agitator: 300 rpm) from the beginning to the termination of revolution.

(D): Fine particles were produced according to the same procedures performed under the same conditions as in (A) except that the amount of water was 600 g.

(E): Fine particles were produced according to the same procedures performed under the same conditions as in (A) except that the amount of water was 1200 g.

Figure 6:
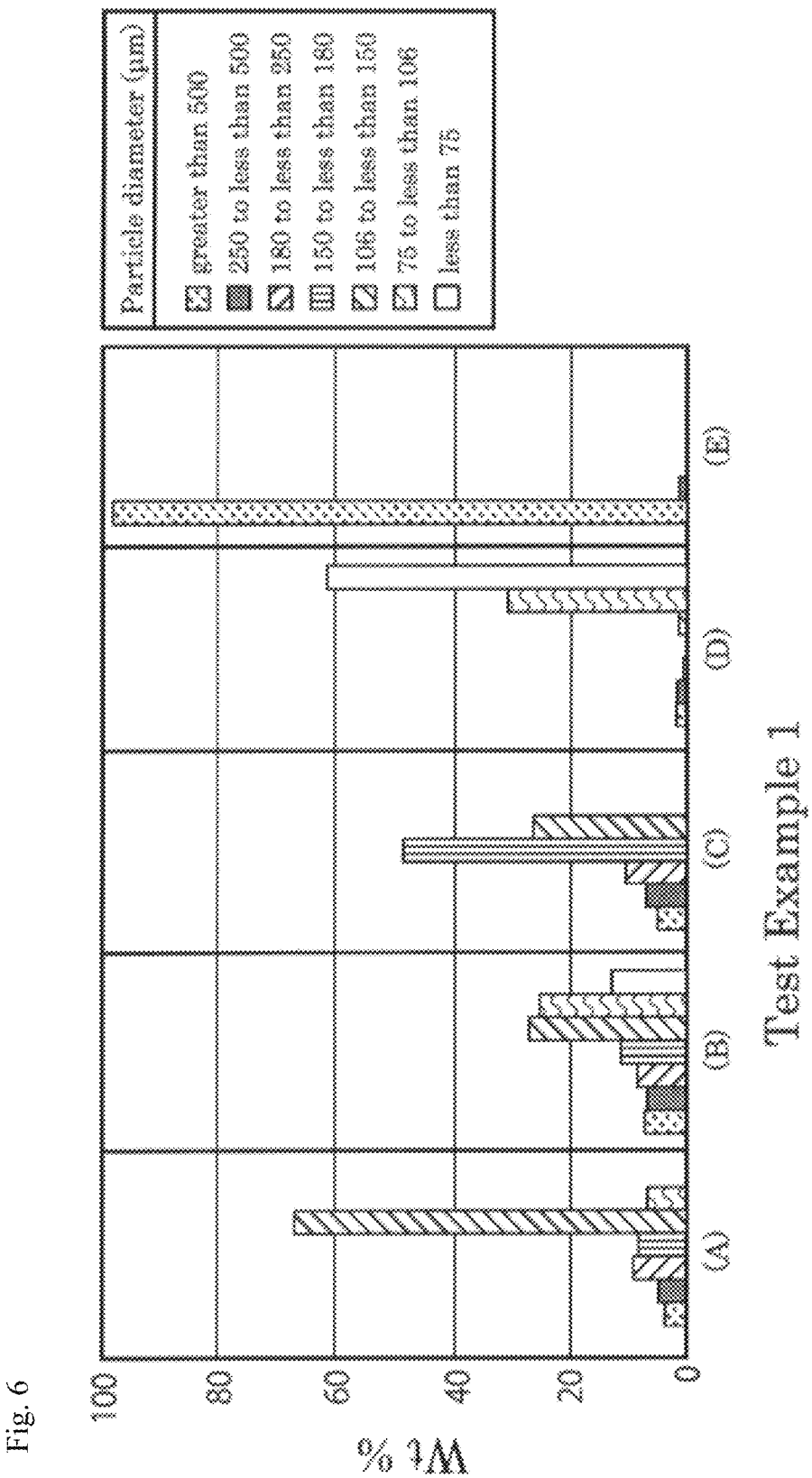
FIG. 6 is a graph showing the particle size distributions of the fine particles obtained in Test Example 1(A) to (E).

FIGS. 1 to 5 show the results of taking micrographs to verify the shape of the respective fine particles obtained in (A) to (E) above. A microscope "Microwatcher" (trade name, manufactured by Keyence Corporation) was used. The micrographs of (A) to (D) were all taken at 175-fold magnification and the micrograph of (E) was taken at 50-fold magnification. FIG. 6 shows the results collected after classifying by sieving the fine particles obtained in (A) to (E) into groups and determining the weight ratio (%) of the fine particles of each group relative to the total particle weight.

The fine particles were compared in terms of shape and FIGS. 1 to 5 clearly show that nearly spherical fine particles were obtained from (A), (C), and (E). Among these, the fine particles obtained in (A) were the most spherical, the fine particles obtained in (C) were the next most spherical, and then the fine particles obtained in (E). On the other hand, spherical fine particles were barely obtained in (B) and (D).

Comparison was made in terms of particle size distribution and FIG. 6 clearly shows that the fine particles obtained in (B) where the peripheral speed of the granulator was 2.1 m/s throughout granulation were significantly varied in particle size, the fine particles obtained in (D) where 60 parts by weight of water was used per 100 parts by weight of microcrystalline cellulose were distributed toward the smaller particle size, and the fine particles obtained in (E) where 120 parts by weight of water was used per 100 parts by weight of microcrystalline cellulose were distributed extremely toward the larger particle size. The fine particles obtained in (C) had a slightly broad particle size distribution, and in (C) granulation tended to progress rapidly due to stirring performed at a high speed from the beginning, making it difficult to control the particle diameter and to produce uniform spherical fine particles with good reproducibility. On the other hand, in (A), management during granulation was easy and high-quality spherical fine particles having a smaller particle diameter and a narrower particle size range was obtained.

Considering the above-described findings comprehensively, the inventors decided to carry out further investigations based on the conditions of (A) where fine particles that had the narrowest particle size distribution and that were nearly spherical were obtained.

Test Example 2

10 kg of microcrystalline cellulose ("Ceolus (registered trademark) PH-101", manufactured by Asahi Kasei Chemicals Corporation) and 8300 g of water were introduced into a high-speed stirring granulator (trade name "high-speed mixer FS-GS-400E" manufactured by Fukae Powtec) and stirred at a peripheral speed of 2.1 m/s (the number of revolutions of the agitator: 26 rpm) for 5 minutes, then at a peripheral speed of 3.6 m/s (the number of revolutions of the agitator: 77 rpm) for 11 minutes, and then at a peripheral speed of 6.6 m/s (the number of revolutions of the agitator: 140 rpm) for 25 minutes.

Figure 7:
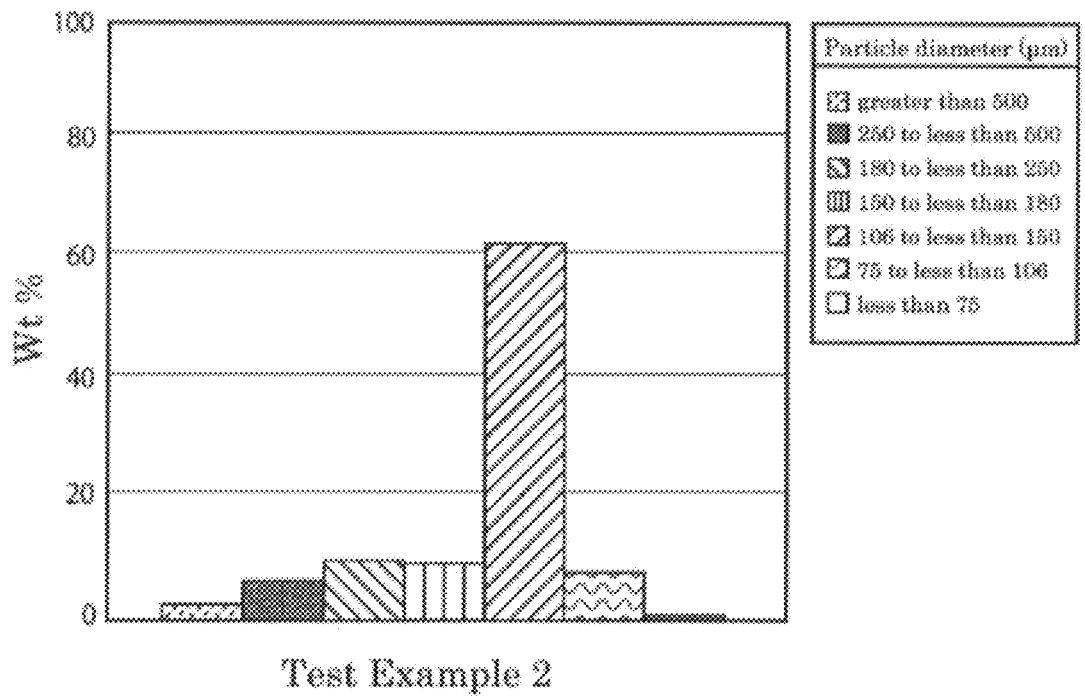
FIG. 7 is a graph showing the particle size distribution of the spherical fine particles obtained in Test Example 2.

Thereafter, the resulting granules were dried with a fluid-bed granulator/dryer at 70° C. for 1 hour, thereby giving fine particles. FIG. 7 shows the results collected after classifying by sieving the resulting spherical fine particles into groups and determining the weight ratio (%) of the fine particles of each group relative to the total particle weight.

As depicted in FIG. 7, it was demonstrated that even when a high-speed mixer of a scale 10 times greater than that of the mixer used in Test Example 1 is used, spherical fine particles having a narrow particle size distribution can be obtained by performing stirring at a low speed until the powdery mixture is uniformly impregnated with water and then performing stirring granulation at a high speed.

Based on the results of Test Examples 1 and 2 above, suitable granulation conditions to obtain spherical fine particles for producing coated fine particles containing tamsulosin hydrochloride were determined to be as follows: The amount of water is within a range of about 70 to about 110 parts by weight per 100 parts by weight of powdery mixture, and the peripheral speed for a high-speed stirring granulator is, in consideration of the type of an apparatus and other influencing factors, within a range of about 1.0 to about 4.0 m/s until a powdery mixture is uniformly impregnated with water and then within a range of about 5.5 to about 9.0 m/s.

Example 1

980 g of microcrystalline cellulose ("Ceolus (registered trademark) PH-101", manufactured by Asahi Kasei Chemicals Corporation), 20 g of tamsulosin hydrochloride, and 815 g of water were introduced into a high-speed stirring granulator (trade name "vertical granulator VG-25", manufactured by Powrex Corporation) and stirred at a peripheral speed of 2.1 m/s (the number of revolutions of the agitator: 100 rpm) for 8 minutes and then at a peripheral speed of 6.3 m/s (the number of revolutions of the agitator: 300 rpm) for 15 minutes.

Figure 8:
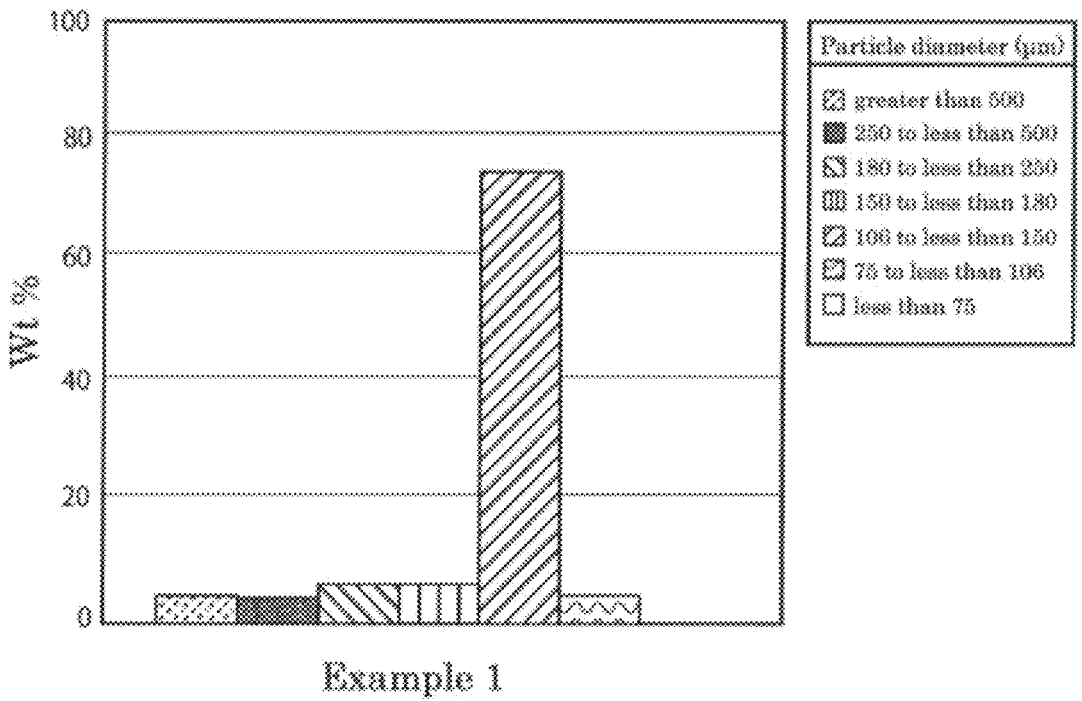
FIG. 8 is a graph showing the particle size distribution of the tamsulosin hydrochloride-containing spherical fine particles obtained in Example 1.

Thereafter, the resulting granules were dried with a fluid-bed granulator/dryer at 70° C. for 1 hour, thereby giving spherical fine particles. Table 1 and FIG. 8 show the results collected after classifying into groups by sieving the resulting spherical fine particles and determining the weight ratio (%) of the fine particles of each group relative to the total particle weight.

TABLE 1

| Particle diameter (μm) | Weight % |
| --- | --- |
| greater than 500 | 4.2 |
| 250 to less than 500 | 3.8 |
| 180 to less than 250 | 6.3 |
| 150 to less than 180 | 6.3 |
| 106 to less than 150 | 75.0 |
| 75 to less than 106 | 4.4 |
| less than 75 | 0.0 |
| Total | 100.0 |

It was demonstrated through Example 1 that tamsulosin hydrochloride-containing spherical fine particles having a very narrow particle size distribution can be obtained according to the present invention.

Example 2

Of the spherical fine particles obtained in Example 1, a sustained-release coating was applied to spherical fine particles having a particle size of 106 to less than 150 μm, thereby giving sustained-release coated fine particles. Coating was performed with a fluid-bed granulator using a 85:15 (in weight ratio) mixture of ethylcellulose and hypromellose dissolved in a concentration of 4 wt % in a 80:20 (in weight ratio) mixed solution of ethanol and water. The resulting coated fine particles entirely passed through a #83 (180 μm) sieve.

These sustained-release coated fine particles were subjected to a fluid-bed coating with a 3:1:1:5 (in weight ratio) mixture of methacrylic acid copolymer LD, an ethyl acrylate-methyl methacrylate copolymer dispersion, an aqueous ethylcellulose dispersion, and water and then dried, thereby giving sustained-release enteric coated fine particles. The resulting coated fine particles entirely passed through a #60 (250 μm) sieve and it was thus demonstrated that sustained-release enteric coated fine particles having a sufficiently small particle size can be obtained according to the present invention.

Example 3

135 parts by weight of the sustained-release enteric coated fine particle obtained in Example 2, 889 parts by weight of D-mannitol, and 125 parts by weight of low-substituted hydroxypropylcellulose were subjected to fluid-bed granulation while intermittently spraying 6 parts by weight of a 2 wt % aqueous hydroxypropylcellulose solution and subjected to a #22 (710 μm) sieve. 30 parts by weight of magnesium aluminometasilicate powder ("Neusilin (registered trademark) UFL2", manufactured by Fuji Chemical Industry Co., Ltd.) and 15 parts by weight of calcium stearate were added to and mixed with the granules that had passed through the sieve, thereby giving powder for tablet pressing. Pressing was performed at a pressure of 6860 N with a rotary press (manufactured by Kikusui Seisakusho Ltd.), giving orally disintegrating tablets having a diameter of 8.5 mm.

Experimental Example 1

A 5 g sample was taken from three random places in the spherical fine particles obtained in Example 1. Then, a 100 mg sample was precisely weighed out from each sample. The tamsulosin hydrochloride content was measured by HPLC and compared with the theoretical value (2 mg of tamsulosin hydrochloride being contained in 100 mg of spherical fine particles). The results showed that the tamsulosin hydrochloride content in each of the three sampled places was 100.1%, 100.5%, or 99.6%, demonstrating that extremely favorable content uniformity is ensured.

INDUSTRIAL APPLICABILITY

The spherical fine particles obtained according to the present invention has a nearly spherical shape, it is easy to apply thereto a sustained-release, enteric, or like coating, and the spherical fine particles remain to be sufficiently small coated fine particles even after being coated, and therefore they can be suitably used in producing an orally disintegrating tablet with which a rough texture is barely felt upon oral administration. Moreover, good content uniformity is ensured with the spherical fine particles even if the tamsulosin hydrochloride content of a pharmaceutical preparation is low, and therefore the spherical fine particles are suitably used in obtaining a high-quality pharmaceutical preparation.

The invention claimed is:

1. A method for producing spherical fine particles comprising tamsulosin hydrochloride, the method comprising the steps of:
   (1) mixing and stirring tamsulosin hydrochloride (a), microcrystalline cellulose (b), and water until a mixture of the component (a) and the component (b) is uniformly impregnated with the water;
   (2) granulating the mixture obtained in step (1) using an stirring granulator whose peripheral speed is set to be 5.5 to 9.0 m/s; and
   (3) drying the granules obtained in step (2);
   wherein spherical fine particles having a particle diameter of from 75 μm to less than 250 μm account for 80 wt % or greater of the entire spherical fine particles obtained.

2. The production method according to claim 1, wherein in step (1), after dry-blending the tamsulosin hydrochloride (a) and the microcrystalline cellulose (b), water is added, and mixing and stirring is performed.

3. The production method according to claim 1, wherein in step (1), mixing and stirring is performed using a stirring granulator whose peripheral speed is set to be 1.0 to 4.0 m/s.

4. The production method according to claim 1, wherein in step (1), the water is added in an amount of 70 to 110 parts by weight per 100 parts by weight of the mixture of the component (a) and the component (b).

5. The production method according to claim 1, wherein spherical fine particles having a particle diameter of from 106 μm to less than 150 μm account for 50 wt % or greater of the entire spherical fine particles obtained.

6. The production method according to claim 1, wherein the obtained spherical fine particles comprise the tamsulosin hydrochloride (a) in an amount of 30 wt % or less.

* * * * *